US006528301B1

(12) United States Patent
Breme et al.

(10) Patent No.: US 6,528,301 B1
(45) Date of Patent: Mar. 4, 2003

(54) PACLITAXEL PRODUCTION BY ACTINOMYCETES

(75) Inventors: Umberto Breme, Vigevano (IT); Marinella Caruso, Parabiago (IT); Nicoletta Crespi Perellino, Milan (IT); Lorena Fedeli, San Damiano di Brugherio (IT); Andrea Pavesi, Buccinasco (IT); Luca Piacenza, San Vittore Olona (IT); Giambattista Ventrella, Milan (IT)

(73) Assignee: Pharmacia & Upjohn SpA, Milan (IT)

( * ) Notice: Subject to any disclaimer, the term of this patent is extended or adjusted under 35 U.S.C. 154(b) by 0 days.

(21) Appl. No.: 09/622,588
(22) PCT Filed: Jan. 21, 1999
(86) PCT No.: PCT/EP99/00417
§ 371 (c)(1),
(2), (4) Date: Aug. 21, 2000
(87) PCT Pub. No.: WO99/42561
PCT Pub. Date: Aug. 26, 1999

(30) Foreign Application Priority Data

Feb. 20, 1998 (GB) .............................................. 9803628
May 7, 1998 (GB) .............................................. 9809767

(51) Int. Cl.⁷ ................................................. C12N 1/20
(52) U.S. Cl. ..................................... 435/252.1; 435/123
(58) Field of Search .............................. 435/123, 252.1

(56) References Cited

U.S. PATENT DOCUMENTS 5,756,536 A * 5/1998 Chen .......................... 514/449

FOREIGN PATENT DOCUMENTS

| WO | 95/04154 | * 2/1995 |
| WO | 96/32490 | * 10/1996 |

* cited by examiner

Primary Examiner—Irene Marx
(74) Attorney, Agent, or Firm—Oblon, Spivak, McClelland, Maier & Neustadt, P.C.

(57) ABSTRACT

The present invention related to microorganisms producing taxanes, such as paclitaxel or related taxanes, to the use of said microorganisms for the production of taxanes, and to the procedure for the isolation of said microorganisms from plants. In particular, the present invention relates to microorganisms of the Actinomycetes group producing taxanes as well as to the biologically pure cultures of a strain of the Actinomycetes group which produces taxanes. The microorganisms of Actinomycetes group are preferably belonging to the suprageneric groups of Streptomycetes, Actinoplanetes, Maduromycetes, Thermomonosporas or Nocardioforms, more preferably they are belonging to genus Streptomyces, Actinoplanes, Nocardiopsis, Micromonospora, Actinomadura or Kitasatosporia, still more preferably to the genus Kitasatosporia. A particularly preferred microorganism is Kitasatosporia sp. CECT 4991.

6 Claims, No Drawings

PACLITAXEL PRODUCTION BY ACTINOMYCETES

This application is a National Stage Application of International Application Serial No. PCT/EP99/00417, filed on Jan. 21, 1999, and claims priority under 35 U.S.C. §119 to GB 9803628.8, filed on Feb. 20, 1998, and GB 9809767.8, filed on May 7, 1998.

The present invention relates to microorganisms producing a taxane, to the use of said microorganisms for the production of a taxane, and to the procedure for the isolation of said microorganisms from plants.

Paclitaxel, a diterpene which is of the chemical structural formula:

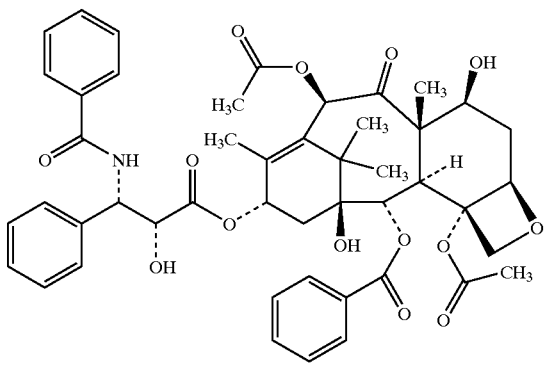

shows significant properties of promoting the polymerization of tubulin and inhibiting the depolymerization of microtubules. For these reasons, paclitaxel is a valuable antileukemic and antitumor agent and is the subject of increasing research. Paclitaxel has been identified in 1971 (Wani M C et al, *J. Amer. Chem. Soc.* 1971, 93, 2325–2327) by isolating it from the bark of *Taxus brevifolia* (Pacific yew). The low yield of the isolation of paclitaxel (around 0.007%) from this source and the concerns about the survival of *Taxus brevifolia*, which is a rather slow growing plant, raised by its massive collection have pushed the research for alternative paclitaxel production methods.

Isolation of paclitaxel from a renewable source such as the needles and the twigs of Taxus species has proven possible although with a yield comparable, if not lower, than that obtainable from the bark of *Taxus brevifolia*.

The total chemical synthesis of paclitaxel has been described by Nicolau et al., *Nature* 1994, 367, 630–634, nevertheless the complexity and low yield of this method have prevented its industrial scale-up.

Semisynthesis of paclitaxel from baccatin III or 10-deacetylbaccatin III, has proved to be a much better option because of the use of a renewable source such as the needles of the European yew *Taxus baccata* to obtain the precursors.

Several documents on tissue culture of plants of the genus Taxus have been published in recent years, however this procedure is limited by the intrinsic technical difficulties of cell culture on an industrial scale.

Recently, patents and patent applications for the production of paclitaxel from the fermentation of fungi and bacteria isolated from samples of Taxus have been published (WO 93/21338, U.S. Pat. No. 5,322,779, WO 95/04154, U.S. Pat. No. 5,561,055 and WO 96/32490). These confirm that there is a need for improved methods for the production of paclitaxel on industrial scale.

In this specification the used classification rules are described in Bergey's Manual of Systematic Bacteriology, vol. 4, 1989.

We have surprisingly found a new taxanes producing microorganism of the Actinomycetes group, which is particularly well suited for an industrial fermentation process for the production of a taxane such as paclitaxel and related taxanes. For instance, compared to the fungi of the prior art, the microorganisms of the present invention can be more easily genetically modified to enhance taxane production and have a shorter fermentation time.

The present invention relates to microorganisms of the Actinomycetes group which produce a taxane, such as paclitaxel or related taxanes, as well as to the biologically pure cultures of a strain of the Actinomycetes group which produce a taxane such as paclitaxel or related taxanes.

The microorganisms of the invention preferably belong to the suprageneric groups of Streptomycetes, Actinoplanetes, Maduromycetes, Thermomonosporas or Nocardioforms, more preferably they belong to the genus Streptomyces, Actinoplanes, Nocardiopsis, Micromonospora, Actinomadura or Kitasatosporia and still more preferably to the genus Kitasatosporia.

A preferred strain according to the present invention is a Kitasatosporia sp. deposited under the Budapest treaty at the Colleccion Española De Cultivos Tipo, (Biological Science Faculty, University of Valencia, 46100 Burjasot (Valencia), Spain) on Jan. 19, 1998 under the deposit number CECT 4991, and it was isolated from a *Taxus baccata* sample and proved to produce paclitaxel or other related taxanes. Therefore, the present invention more preferably relates to the biologically pure cultures of the genus Kitasatosporia having all the identifiying characteristics of Kitasatosporia sp. CECT 4991.

Moreover, the present invention provides a procedure for the isolation of microorganisms of the Actinomycetes group which produce a taxane, such as paclitaxel or related taxanes, from plants, including plants of the Taxus genus and related genera, collected from various geographical area.

Preferably, the isolation procedure of microorganisms according to the present invention is carried out on plants selected from plants of Taxus genus or related genera, more preferably *Taxus baccata, Taxus brevifolia,* or *Torreja californica*.

According to the present invention, the procedure for the isolation of microorganisms of the Actinomycetes group producing a taxane, such as paclitaxel or related taxanes, may be carried out, for example, by sterilizing each part of the plant (roots, bark, twigs, needles, stems) with a sterilizing agent, preferably selected from sodium hypochlorite, propylenoxid, a solution of dodecylcarbamylmethylbenzyldimethylammonium cloride, triethilenglycol sodium nitrite and UV light, by cutting the different parts of the plant in small fragments with a sterile blade and by placing these small fragments on agar culture media in Petri plates or, preferably, by homogenizing the sterilized parts as above, with a blender at room temperature; the resultant homogenate, reduced to powder may be then transferred on agar culture media in Petri plates using a modified Andersen's sampler. The microorganism colonies grown on the agar plates are then removed and transferred to plates containing water agar media until a pure culture is obtained.

The colonies were grown in liquid media suitable for growth and taxane production, such as conditions suitable for paclitaxel production. The extracts and the fractions obtained from the production cultures can be tested to determine the presence of taxanes, such as paclitaxel or related taxanes, using suitable assays.

In the more preferred procedure for the isolation of the microorganisms of the Actinomycetes group from Taxus and related plants, the powdered samples obtained as above described are introduced into a modified Andersen's sampler, an apparatus used to analyze the microorganisms population in air samples. Andersen's sampler is described in detail in: A. Andersen, *Journal of Bacteriology* 1958, 76 (5), 471–484. This sampler is modified by associating it with a sedimentation chamber in which the powdered samples are introduced. The sedimentation chamber allows isolation of microorganisms present in low percentage from soil and vegetable powdered samples. It consists of a cylindric box made of plexiglass connected to the sampler by a rubber tubing. Plates containing different isolation media were placed in the sampler and the powdered samples were drawn. Depending on their aerodynamic dimensions, the microorganisms present in the powdered samples were collected on plates containing different isolation media. The plates are then removed, incubated and examined. The colonies of microorganisms of the Actinomycetes group grown on the agar plates were picked up and transferred on water agar media in Petri plates until a pure culture was obtained. This method enables the isolation of microorganisms of the Actinomycetes group well separated from fungi and other bacteria.

A further object of the invention is the use of said microorganisms of the Actinomycetes group for the production of a taxane, such as paclitaxel or related taxanes, which comprises the steps of a) culturing a microorganism of the Actinomycetes group producing the taxanes in a liquid media suitable for its growth and production b) recovering the taxanes produced.

Thus the invention provides a biologically pure culture of a microorganism of the invention. Such a culture may be substantially free of other microorganisms. The term "related taxanes" is intended to include paclitaxel and all taxane skeleton-containing compounds, which includes taxane skeleton-containing compounds thought to be precursors in the biosynthesis, for example baccatin III, 10-deacetyl baccatin III, cephalomannine, 10-daecetylcephalomannine. The term also includes deacetyltaxol, 7-xylosyltaxol, 7-epi-10-deacetyltaxol, 7-xylosyl-10-deacetyltaxol, 7-epi-taxol and 7-epi-10-deacetylbaccatin III.

The term "related taxanes" also includes taxanes which are recognised by an antibody produced to paclitaxel, 10-deacetyltaxol, 7-xylosyltaxol, 7-epi-10-deacetyltaxol, 7-xylosyl-10-deacetyltaxol, 7-epi-taxol, 7-epi-10-deacetylbaccatin III, baccatin III, 10-deacetyl baccatin III, cephalomannine or 10-deacetylcephalornannine. Such antibodies can be polyclonal antibodies or monoclonal antibodies. Polyclonal antibodies can be produced using standard techniques, such as immunising a host animal with paclitaxel, 10-deacetyltaxol, 7-xylosyltaxol, 7-epi-10-deacetyltaxol, 7-xylosyl-10-deacetyltaxol, 7-epi-taxol, 7-epi-10-deacetylbaccatin III, baccatin III, 10-deacetyl baccatin III, cephalomannine or 10-deacetylcephalomannine and obtaining the polyclonal antibodies from the animal, for example from the serum. Monoclonal antibodies can also be produced by standard techniques, such as the method of producing monoclonal antibodies of Kohler and Milstein (Nature 256, 495–497 (1975)). To produce such antibodies using the Kohler and Milstein method paclitaxel, 10 deacetyltaxol, 7-xylosyltaxol, 7-epi-10-deacetyltaxol, 7-xylosyl-10-deacetyltaxol, 7-epi-taxol, 7-epi-10-deacetylbaccatin III, baccatin III, 10-deacetyl baccatin III, cephalomannine or 10-deacetylcephalomannine would be used to immunise the animal. In particular, "related taxanes" includes those recognised by the antibody R4, 8A10, 3C6 or 3H5. These antibodies are available in kits from Hawaii Biotechnology Group Inc. Preferred "related taxanes" are those which have an IC50 (concentration of taxane required to inhibit the binding of the antibody to solid phase antigen, which may be paclitaxel or baccatin III, by 50% in a competitive immunoassay) of less than 500 nM, less than 250 nM, less than 100 nM, less than 50 nM, or less than 10 nM, as measured using a competitive immunoassay kit, such as from Hawaii Biotechnology Group Inc.

To grow the isolated colonies the following culture media can be used: water agar, Czapek agar, ISP medium 2 (*International Streptomyces Project,* Shirling E. B. and Gottlieb D., *Int. J. Syst. Bacteriol.* 1966, 16, 313–340) adding antifungal and antibacterial substances. The microorganism colonies grown on the agar plates are removed and transferred to water agar media in Petri plates until a pure culture is obtained. After purification, the colonies of the Actinomycetes group producing taxanes, such as paclitaxel or related taxanes, are transferred into tube of ISP medium 3.

Each isolated microorganism can be stored either in glycerol at −80° C. or lyophilized. A suitable medium for culturing on organism of the invention may be one which comprises an assimilable carbon source, an assimilable nitrogen source and inorganic salts.

Each microorganism of the Actinomycetes group producing taxanes, such as paclitaxel and related taxanes, may be cultured into liquid seed media, containing complex carbon and nitrogen sources, in Erlenmyer flasks and incubated on a shaker at temperatures ranging from 22° to 30° C. and at agitation rates from 150 to 250 rpm for 24–48 hours. At the end of incubation, the seed culture is inoculated into different production media containing complex substances such as carbon sources (starch, dextrin, morsuit), nitrogen sources (corn-steep liquor, soybean meal, caseine, soytone, yeast extract), ammonium salts (ammonium sulfate, ammonium chloride) and mineral salts; calcium carbonate and potassium phosphate can be useful. The temperature of incubation can range from 22° to 32° C. and the agitation rate from 150 to 250 rpm. After inoculation, the fermentation production media are incubated over a period of 2 to 8 days.

After the required incubation time, the cultures are centrifuged and the pellet separated from the supernatant. The supernatant of the culture can be extracted with an organic solvent unmixable with water, for example dichloromethane.

Preferably the supernatant of the culture is loaded onto a pre-packed diatomaceous earth column. This material allows efficient liquid-liquid extraction of lipophilic compounds from aqueous solutions without emulsion problems. Taxanes, such as paclitaxel and other taxanes can be recovered from the column with various organic solvents.

The mycelium cake of the culture can be extracted by homogenizing it with an organic solvent, for example methanol.

Preferably, after homogenizing the mycelium of the culture with a solvent, for example methanol, the pellet is removed by centrifugation, while the solvent extract is dried in vacuo, reconstituted with a small volume of methanol and then with water.

This solution can be loaded onto pre-packed diatomaceous earth columns and treated as the supernatant of the culture.

The fermentation of the isolated microorganisms can be scaled up using fermenter tanks. For instance in order to prepare the inoculum for a 500 L fermenter, the actinomycetes can be cultured in liquid seed media, containing complex substances such as carbon sources (starch, dextrin, morsuit), nitrogen sources (corn-steep liquor, soybean meal, caseine, soytone, yeast extract), ammonium salts (ammonium sulfate, ammonium chloride) and mineral salts; calcium carbonate and potassium phosphate can also be useful.

The temperature of incubation can range from 22° to 32° C. and the agitation rate from 150 to 250 rpm for 24–48 hours.

At the end of incubation (24 to 48 hours) the seed culture is transferred into an intermediate fermenter containing the same liquid medium as previously described and incubated for 24 to 48 hours at a temperature ranging from 22° to 32° C., at an agitation rate ranging from 150 to 250 rpm and with an appropriate air flow rate, for instance 68 nL/min for 24–48 hours. Finally a portion of this culture is transferred to the final tank, for example a 500 L fermenter, with a medium containing complex substances such as carbon sources (starch, dextrin, morsuit), nitrogen sources (corn-steep liquor, soybean meal, caseine, soytone, yeast extract), ammonium salts (ammonium sulfate, ammonium chloride) and mineral salts, calcium carbonate or potassium phosphate. After a fermentation period ranging between 96 and 176 hours, the mycelium is removed from the culture by centrifugation and the clear supernatant applied onto a column of chromatographic resin, for instance Amberlite XAD-2.

After the adsorption, the resin can be eluted with solvents, for example ethanol and after removal of the organic solvent under reduced pressure the fractions eluted from the column are extracted with organic solvents unmixable with water such as dichloremethane.

The solvent extract can be purified using reversed-phase C18 columns that are eluted using a step gradient of an alcohol, for example methanol, in water.

A further purification of paclitaxel can be achieved by means of others chromatographic procedures, for example preparative HPLC on RP18 or pentafluorophenyl columns. The extracts and the fractions obtained with the described procedures can be tested to determine the amounts of taxane, such as paclitaxel or related taxanes using suitable assays.

Such an assay may comprise recognition of the taxane by an antibody to a taxane, such as an antibody to paclitaxel, 10 deacetyltaxol, 7-xylosyltaxol, 7-epi-10-deacetyltaxol, 7-xylosyl-10-deacetyltaxol, 7-epi-taxol, 7-epi-10-deacetylbaccatin III, baccatin III, 10-deacetyl baccatin III, cephalomannine or 10-deacetylcephalomannine.

Preferably two enzyme immunoassay kits (Indirect Competitive Inhibition Enzyme Immunoassay—CIEIA) employing, respectively, a polyclonal antibody against a taxane skeleton-containing compound and a monoclonal antibody against paclitaxel, are used. Immunoassays and antibodies for paclitaxel can be obtained from Hawaii Biotechnology Group Inc.

Extracts may be analyzed by HPLC, for example on a reversed-phase C18 column using an acetonitrile—water gradient and using a standard curve of paclitaxel concentration versus peak area to quantify paclitaxel in samples.

A further evidence for production of paclitaxel by the isolated strains can be obtained in feeding experiments with radioactive precursors for example with L-[2,3,4,5,6-$^3$H] phenylalanine and $^3$H-Baccatin and also analytically by liquid chromatography coupled to mass spectroscopy (LC-MS) of the paclitaxel isolated from the cultures. The isolated microorganisms of the Actinomycetes group producing a taxane, such as paclitaxel or related taxanes, can be genetically modified, for example by random mutagenesis or biosynthetic gene manipulation, to enhance taxane production.

The taxane produced by the microorganisms of the invention may act as antitumour agents. A human or animal suffering from a tumor may thus be treated by a method which comprises the administration thereto of an effective amount of such a taxane. The condition of the human or animal may thereby be improved.

Examples of tumors that can be treated are sarcomas, carcinomas, lymphomas, neuroblastomas, melanomas, myelomas, Wilms tumor, leukemias and adenocarcinomas. The taxane can be used to treat ovarian cancer, platinum-resistant ovarian cancer, metastatic breast cancer, non-small cell lung cancer, and head and neck cancer. The taxane may be used to produce a pharmaceutical composition which comprises, as active ingredient, the taxane and a pharmaceutically acceptable carrier or diluent. This composition is usually prepared following conventional methods and is administered in a pharmaceutically suitable form.

Administration can be made by any of the accepted ways for administration of antitumor agents such as intravenous, intramuscular or subcutaneous injection or topical application. For systemic injection the active compound may be, for example, dissolved in a vehicle consisting of a mixture of polyoxyethlated castor oil (Chremophor EL) 50% and ethanol 50% and then diluted with glucose 5% solution at the desired concentration, or in other pharmaceutically suitable carriers.

The amount of the active compound administered depends on the treated subject, age, weight, sex etc., and the severity of the affliction. The method of administration depends on the judgement of the prescribing physician. A suitable dosage for an average 70 kg person may range from about 0.01 g to about 1 g per day.

The following Examples illustrate the invention:

Table 1: this table reports the plants from which samples were collected, the procedures for the isolation of microorganism of the Actinomycetes group producing taxanes, such as paclitaxel and related taxanes and the genus of the isolated microorganisms of the Actinomycetes group, as described in Examples 1 to 9;

Table 2: cultural and morphological characteristics on different culture media of strain Kitasatosporia sp. CECT 4991.

Table 3: Carbohydrate utilization by strain Kitasatosporia sp. CECT 4991.

Table 4: Enzymatic activities of strain Kitasatosporia sp. CECT 4991.

Table 5: Purification procedure of the extract obtained from the culture of strain Kitasatosporia sp. CECT 4991 incubated with L-[2,3,4,5,6-$^3$H]phenylalanine

EXAMPLES 1–9
Isolation of Microorganisms of the Actinomycetes Group Producing Taxanes, Such as Paclitaxel and Related Taxanes With the method of the invention, 70 different microorganisms of the Actinomycetes group were isolated and demonstrated to produce paclitaxel or related taxanes according to the above described enzyme immunoassay.

A series of nine examples are reported below. The detailed information of each isolation related to the plants, to methods of pretreatment, to isolation media and to isolated actinomycetales are shown in the table 1.

The surface of each part of the plant (roots, bark, twigs, needles, stems) was sterilized with either sodium hypochlorite or propylenoxid or a solution of dodecylcarbamylmethyl-benzyldimethylammonium chloride triethilenglycol sodium nitrite (IPIT) or UV light. The sample was homogenized with a blender at room temperature, reduced to powder and introduced into a sedimentation chamber connected to an Andersen's sampler.

Andersen's sampler is described in detail in: A. Andersen, *Journal of Bacteriology* 1958, 76 (5), 471–484. The sampler used for the present invention has been modified by associating it with a sedimentation chamber in which the powdered samples are introduced. The sedimentation chamber consists of a cylindric box made of plexiglass connected to the sampler by a rubber tubing. The powdered sample was introduced in the sedimentation chamber by a hole situated in the upper side. The sample was then dispersed by the action of a fan placed in the chamber operating for 30 seconds. After 10 minutes and then again after one hour of sedimentation, the sample was drawn into the Andersen's sampler and collected on the agar plates placed in the instrument. The plates containing different isolation media were then removed, inverted in their covers, incubated at 28° C. and examined on a day-to-day basis. The colonies of microorganisms of the Actinomycetes group grown on the agar plates were removed and transferred to water agar until a pure culture was obtained. After purification, the microorganisms of the Actinomycetes group producing paclitaxel or related taxanes were transferred into tubes of ISP medium 3.

The strain Kitasatosporia sp. CECT 4991 isolated in Example 3 was further characterized as described in the following examples.

EXAMPLE 10
Characterization of the Strain Kitasatosporia sp. CECT 4991
Culture and Morphological Characteristics Culture characteristics of the strain were determined after 7, 14 and 21 days incubation on the following culture media: 2.5% water agar, yeast extract-malt extract agar (ISP medium 2), oatmeal agar (ISP medium 3), inorganic salts-starch agar (ISP medium 4), glycerol asparagine agar (ISP medium 5), tyrosine agar (ISP medium 7), Nutrient agar, Bennett's agar and Bacto Czapek solution agar. The culture features of the strain Kitasatosporia sp. CECT 4991 are shown in Table 2. The strain grows well on all organic and synthetic media and the colonies are covered with gray aerial mycelium and spores. Absence of melanoid pigment on ISP medium 7. Morphological observations were assessed by light and scanning electron microscopy on cultures grown at 27° C. for 14 days on ISP medium 3, Nutrient agar, Czapek agar and 2.5% water agar. The substrate mycelium is well developed with hyphae densely branched, 0.5–0.8 μm in diameter. Aerial hyphae bear long spore chains of more than 20 spores. The spores are globose, oblong of irregular length (0.8–1.8×0.8–1.2 μm) with smooth surface. Spore chains are long, straight or slightly flexuous unbranched or poorly irregularly branched.

Physiological Tests

Carbohydrate utilization was carried out by the API 50 CH system (BioMèrieux SA) using as inoculum a 3% agar medium (yeast nitrogen base) neutralized with 20% (v/v) 1% K$_2$HPO$_4$ solution. The results are summarized in Table 3. Enzymatic activities were carried out by the API ZYM system (BioMerieux SA). Enzymatic activities of the strain are shown in Table 4.

Cell Chemistry

Determination of the cell-wall composition, including diaminopimelic acid isomers and sugars, was carried out according to Becker et al, *Appl. Microbiol.* 1965, 13, 236–243. Cell wall containing meso-diaminopimelic acid and whole-cell hydrolysates is characterized by the presence of galactose and by the absence of madurose, arabinose and xylose. On the basis of that, the cell wall analysis was repeated according to Omura et al, *J. Antibiotic,* 1981, 34, 1633–1634. The analysis of the cell wall showed L-diaminopimelic acid in aerial spores and meso-diaminopimelic acid in vegetative mycelia. These results suggested that the strain CECT 4991 belongs to the genus Kitasatosporia.

EXAMPLE 11
Flask Fermentation of the Strain Kitasatosporia sp. CECT 4991

A frozen vial of the strain Kitasatosporia sp. CECT 4991 was defrosted and transferred in 300 mL Erlenmyer flask containing 30 mL of the following liquid seed medium (VS): corn steep liquor 10 g/L, caseine 10 g/L, dextrin 20 g/L, (NH$_4$)$_2$SO$_4$ g/L, CaCO$_3$ 5 g/L, K$_2$HPO$_4$ 0.1 g/L, deionized water to 1000 mL. The flask was incubated under aerobic condition for 48 hours at 28° C., 250 rpm, 70% humidity. At completion of the incubation, 2 mL aliquot was used to inoculate aseptically a 300 mL Erlenmyer flask containing 50 mL of the following liquid productive medium (PT): morsuit 25 g/L, dextrin 10 g/L, soytone 15 g/L, MOPS 5 g/L, $K_2HPO_4$ 0.5 g/L, $FeSO_4.7H_2O$ 10 mg/l, $MnSO_4.H_2O$, 10 mg/L, $ZnSO_4.7H_2O$ 10 mg/L, $MgSO_4.7H_2O$ 10 mg/L. The flask was incubated under aerobic condition for 168 hours at 28° C., 250 rpm, 70% humidity.

Extraction of Culture

After the required 168 hours incubation time, the culture was centrifuged at 5000 g for 20 min and the pellet set apart for a separate extraction while 20 mL of the culture supernatant were loaded onto a pre-packed Extrelut 20 (diatomaceous earth) column (E. Merck, Germany).

After the application of the culture, the column was washed with n-hexane (120 mL) to remove the fatty components of the culture and then with dichloromethane (80 mL) to recover paclitaxel and other taxanes from the column. The dichloromethane extract was then brought to dryness to be tested by the immunoenzymatic assay (CIEIA). The mycelium cake of the culture was extracted by homogenizing it with 10 mL of methanol. After separating the pellet by centrifugation at 5000 g for 30 min., the supernatant was dried in vacuo, reconstituted in methanol (500 $\mu$L) and taken to a final volume of 20 mL with water. This solution was then treated as the supernatant.

Indirect Competitive Inhibition Enzyme Immunoassay (CIEIA)

The dried dichloromethane extracts were dissolved in 100 $\mu$L of phosphate buffered saline (PBS) containing 0.25% (w/v) BSA, 0.05% Tween 20 and 20% methanol (PBS-T-M) to obtain 200×concentrated samples.

The suspended extracts were serially diluted in PBS-T-M and tested to determine the amounts of taxanes and paclitaxel using two kinds of enzyme immunoassay kits employing a polyclonal antibody against a taxane skeleton-containing compound and a monoclonal antibody against paclitaxel, respectively.

All samples tested by CIEIA were run in duplicate and the mean result of each set of replicates was calculated.

A standard curve was constructed using a set of taxol standard dilution. As a result, it was found that the supernatant contained 1.4 $\mu$g of paclitaxel from 1 liter of culture while the mycelium contained about 160 ng of paclitaxel from 1 liter of culture.

EXAMPLE 12

Endogenous Paclitaxel Production Demonstration by Fermentation with Radioactive Precursors A further evidence for production of paclitaxel by the strain Kitasatosporia sp. CECT 4991 has been obtained in two feeding experiments with radioactive precursors.

Feeding Experiment with L-[2,3,4,5,6-$^3$H]phenylalanine

A frozen vial of the strain Kitasatosporia sp. CECT 4991 was defrosted and transferred in 300 mL Erlenmyer flask containing 30 mL of the following liquid seed medium VS. The flask was incubated under aerobic condition at 28° C. and 250 rpm. After 48 hours of incubation the labeled precursor L-[2,3,4,5,6-$^3$H]phenylalanine (120 $\mu$Ci, specific activity 5.11 TBq/mmol) was fed to the microorganism. After additional 48 hours, the culture was centrifuged (30 minutes at 3000×g) and the mycelium was extracted three times with MeOH. The organic solvent was evaporated under reduced pressure and the aqueous residue was loaded onto two Extrelut 20 columns. The clear supernatant of the culture was loaded onto three Extrelut 20 columns. Each column was extracted with 120 mL of n-hexane (discarded), then with 80 mL of $CH_2Cl_2$, as previously described. The $CH_2Cl_2$ extracts were combined, dried under reduced pressure and to this crude extract of taxanes were added unlabeled Baccatin III and paclitaxel, 10 $\mu$g each. This extract was then subjected to the chromatographic procedure of Table 5.

The incorporated radioactivity, even though rather low, is significant because the recovery of unlabeled baccatin allows exclusion of the possibility that paclitaxel could be labeled by exchange with the tritiated water eventually present in the medium.

Feeding Experiment with $^3$H-Baccatin

A frozen vial of the strain Kitasatosporia sp. CECT 4991 was defrosted and transferred in 300 mL Erlenmyer flask containing 30 mL of the following liquid seed medium VS. The flask was incubated under aerobic condition for 48 hours at 28° C., 250 rpm. At completion of the incubation, 2 mL aliquot was used to inoculate aseptically a 300 mL Erlenmyer flask containing 50 mL of the following liquid productive medium PT. The flask was incubated under aerobic condition at 28° C., 250 rpm. After 24 hours of incubation the labeled precursor $^3$H-Baccatin (20 $\mu$Ci, specific activity 1.83 MBq/mg) was fed to the microorganism.

After additional 144 hours, the culture was centrifuged (30 minutes at 3000×g) and the clear supernatant was loaded onto two Extrelut columns. Each column was extracted with 100 mL of n-hexane (discarded), then with 100 mL of $CH_2Cl_2$. The crude extract of taxanes was dried under reduced pressure, added with unlabelled paclitaxel, 50 $\mu$g, then submitted to the following chromatographic procedure:

the crude $CH_2Cl_2$ extract was purified by chromatography on TLC in system a)

the band corresponding to paclitaxel was scraped, eluted and concentrated the extract of the band was submitted to a second chromatography in solvent b)

the band corresponding to paclitaxel was scraped, eluted and concentrated one half of the band containing paclitaxel was injected in HPLC and the radioactivity corresponding to peak of paclitaxel was determined by liquid scintillation.

the second half of the band was diluted to a theoretical concentration of 125 $\mu$g/mL. The quantity of paclitaxel present in this solution was determined by HPLC analysis in comparison with a calibration curve.

The radioactivity incorporated into the molecule of paclitaxel was 1.26 nCi/50 mL of culture, corresponding to an incorporation of 510 ng/L of baccatin III and to a production of 742 ng/L of paclitaxel.

The recovery of the added unlabelled paclitaxel corresponding to 73%, the final estimated production of paclitaxel was of 942 ng/L.

HPLC Analysis

HPLC analysis were performed on a reversed-phase C18 column—5 $\mu$m–25×0.46 cm using the following elution program:

from 0 to 20 minutes isocratic at 30% HPLC grade acetonitrile in Milli-Q grade water, from 20 to 25 minutes linear gradient from 30% to 50% acetonitrile in water, from 25 to 40 minutes isocratic at 50% acetonitrile in water.

The column was thermostated at 32° C. and eluted at a flow rate of 2 mL/min.

A standard curve of paclitaxel concentration versus peak area was used to quantify paclitaxel in samples.

EXAMPLE 13
Production of Paclitaxel in Fermenter

For the first stage of the seed phase four well-grown agar slants of Kitasatosporia sp. CECT 4991 were used to inoculate into eight 2 L baffled glass bottles containing 500 mL of the medium VS. For the second stage of seed phase the baffled glass bottles were incubated at 28° C., for 48 hours on a rotary shaker (130 rpm). At the end of incubation, the seed cultures obtained were pooled and 3.5 L of this pool were transferred into a 200 L fermenter containing 100 L of the same media VS. The process was carried out at 28° C., for 48 hours, with agitation at 150 rpm remote control and air flow at a rate of 68 mL/min. A 15 L portion of the vegetative culture by fermenter was inoculated into a 500 L fermenter containing 300 L of the following productive media: morsuit 25 g/L, dextrin 10 g/L, soytone 15 g/L, MOPS 5 g/L, $K_2HPO_4$ 0.5 g/L. After 120 hours of incubation, the mycelium was removed from the culture by continuous centrifugation with a centrifugal separator and the clear supernatant applied onto a XAD-2 column (30 L) previously washed with NaOH 1N (30 L), water (30 L), HCl (30 L), water (30 L), acetone (60 L), water (90 L).

After the adsorption, the resin was washed with 90 L of water (discarded) and eluted with ethanol (60 L). The ethanol extract was concentrated under reduced pressure to a volume of 10 L and extracted twice with n-hexane (discarded) and twice with dichloremethane. The dichloromethane crude extract was brought to dryness, re-suspended to a 30 mL volume with methanol and partially purified according to the procedure described by Mattina. M. J .I. and MacEachern. G. J. (*J. Chrom. A* 1994, 679, 269–275) using C18 disposable cartridges containing 10 g of sorbent. Prior to use, the cartridge was conditioned with 100 mL ethyl acetate, 100 mL methanol and 100 mL of Milli-Q grade water taking care of leaving at least 1 cm of water above the top frit of the cartridge before loading an aliquot of 6 mL of the crude extract. The cartridge was eluted with 50 mL of Milli-Q grade water, 100 mL of 20% methanol, 100 mL of 50% methanol, 100 mL of 80% methanol and 100 mL of methanol. The polyclonal antibody assay indicated that all taxanes had selectively been eluted from the cartridge in the 80% methanol while the monoclonal antibody assay indicated a production of 2 $\mu$g/L of paclitaxel referred to the original culture volume (300 L).

2 mL of the paclitaxel containing fraction were brought to dryness, resuspended in 20 $\mu$L of methanol and further purified by HPLC under the conditions described herein. Fractions were collected every minute from the outlet of the HPLC system; the resulting 40 fractions were monitored for paclitaxel content with the monoclonal antibody assay, as described above, that evidentiated paclitaxel in one single fraction eluted from the HPLC column between 27 and 28 minutes with an estimated concentration of 1.3 $\mu$g/L referred to the original culture volume (300 L).

LC-MS Detection of Paclitaxel

The same sample was subjected to RP-HPLC using a 2.0×250 mm, pentafluorophenyl 5 $\mu$m column. Mobile phases A and B were respectively:

Phase A: Milli-Q grade water containing 0.1% of acetic acid glacial, 99.99%

Phase B: acetonitrile HPLC grade containing 0.04% of acetic acid glacial, 99.99%.

Elutions were carried out with a steps gradient of B from 46.7% to 57.3% in 47 minutes at a flow rate of 0.165 mL/min. Separations were performed at room temperature and elution profiles were monitored with a diode array detector at the wavelength of 227 nm.

On-line RP-HPLC/electrospray mass spectrometry was performed on a single quadrupole instrument equipped with an electrospray interface.

Eluates from RP-HPLC were directly injected into the ion source of the mass spectrometer. The electrospray potential was approx. 6 kV. The quadrupole mass analyzer was set up to scan over a mass-to-charge ratio (m/z) from 150 to 920 Da, at 0.5 s per scan. The sum of data acquired constitued the final spectrum. Mass calibration was performed with a mixture of valine, tri-tyrosine and hexa-tyrosine.

LC-MS analysis of this fraction confirmed the presence of paclitaxel by evidentiating a peak with the same RT (24.13 minutes, under the conditions reported in this section), UV spectrum and mass spectrum of paclitaxel. The concentration of paclitaxel determined by HPLC in comparison with a paclitaxel calibration curve, corresponded to 1 $\mu$g/L referred to the total volume of the culture (300 L).

TABLE 1

| Example | Plant | Sample | Method of pretreatment | Isolation agar | Antibiotics incorporated (mg/L) | Number of strains and related genus |
|---|---|---|---|---|---|---|
| 1 | Taxus baccata | inner bark | IPIT 100% | WA, CYA | Cycloheximide (60) penicillin (10) | 1 Streptomyces 2 Actinoplanes 3 unidentified |
| 2 | Taxus baccata | inner bark | IPIT 50% | WA, ISP2 | Cycloheximide (60) polimixin (5) | 1 Streptomyces |
| 3 | Taxus baccata | bark | IPIT 100% | WA | Cycloheximide (60) | 6 Streptomyces 1 Nocardiopsis 1 Kitasatosporia |
| 4 | Taxus baccata | needles | UV light | WA | Cycloheximide (60) nystatin (60) tunicamicin (30) | 4 Streptomyces 8 Micromonospora 1 unidentified |
| 5 | Taxus brevifolia | twigs | propylenoxid | WA, CYA | cycloheximide (60) nalidix acid (15) | 2 Streptomyces 1 Micromonospora |

TABLE 1-continued

| Example | Plant | Sample | Method of pretreatment | Isolation agar | Antibiotics incorporated (mg/L) | Number of strains and related genus |
|---|---|---|---|---|---|---|
| 6 | Torreja californica | twigs | propylenoxid | WA | cycloheximide (60) nystatin (60) | 6 Streptomyces |
| 7 | Taxus baccata | roots | sodium hypochlorite | WA, ISP2 | cycloheximide (60) tetracycline (10) | 4 Streptomyces 1 Actinomadura |
| 8 | Taxus baccata | stem | | WA | cycloheximide (60) tunicamicin (30) | 2 Streptomyces 1 Actinomadura |
| 9 | Taxus baccata | bark | UV light IPIT 30% | WA, CYA | cycloheximide (60) novobiocin (25) | 20 Streptomyces 1 Nocardioforme 4 unidentified |

WA = water agar;
CYA = Czapek agar

TABLE 2

| MEDIA | GROWTH | AERIAL MYCELIUM | SUBSTRATE MYCELIUM | PIGMENT |
|---|---|---|---|---|
| WA25 | ++ | gray | colourless | – |
| ISP MEDIUM 2 | +++ | gray | brown | – |
| ISP MEDIUM 3 | +++ | gray | gray | – |
| ISP MEDIUM 4 | +++ | gray | beige | – |
| ISP MEDIUM 5 | +++ | gray | light gray | – |
| ISP MEDIUM 7 | +++ | gray | light gray | – |
| NUTRIENT AGAR | +++ | gray | white | – |
| BENNETT'S AGAR | +++ | gray | beige | – |
| CZAPEK AGAR | +++ | gray | gray | – |

TABLE 3

| CARBOHYDRATE | |
|---|---|
| Glycerol | + |
| Erythritol | – |
| D-Arabinose | – |
| L-Arabinose | – |
| Ribose | – |
| D-Xylose | + |
| L-Xylose | – |
| Adonitol | – |
| β-Methyl-D-xyloside | – |
| Galactose | + |
| Glucose | + |
| Fructose | – |
| Mannose | + |
| Sorbose | – |
| Rhamnose | – |
| Dulcitol | – |
| Inositol | – |
| Mannitol | – |
| Sorbitol | – |
| α-Methyl-D-mannoside | – |
| α-Methyl-D-glucoside | – |
| N-Acetyl-glucosamine | + |
| Amygdalin | + |
| Arbutin | + |
| Esculin | – |
| Salicin | ± |
| Cellobiose | + |
| Maltose | + |
| Lactose | – |
| Melibiose | – |
| Sucrose | + |
| Trehalose | + |
| Inulin | – |
| Melezitose | – |
| Raffinose | – |
| Starch | + |
| Glycogen | + |
| Xylitol | – |
| Gentiobiose | + |
| D-Turanose | – |
| D-Lyxose | – |
| D-Tagatose | – |
| D-Fucose | – |
| L-Fucose | – |
| D-Arabitol | – |
| L-Arabitol | – |
| Gluconate | + |
| 2 Keto gluconate | – |
| 5 Keto gluconate | – |

TABLE 4

| ENZYME ASSAYED FOR | |
|---|---|
| Phosphatase alcaline | + |
| Esterase (C 4) | + |
| Esterase Lipase (C 8) | + |
| Lipase (C 14) | – |
| Leucine arylamidase | + |
| Valine arylamidase | – |
| Cystine arylamidase | – |
| Trypsin | – |
| Chymotrypsin | – |
| Phosphatase acid | + |
| Naphthol-AS-B1-phpsphohydrolase | + |
| α-galactosidase | – |
| β-galactosidase | + |
| β-glucuronidase | – |
| α-glucosidase | – |
| β-glucosidase | + |
| N-acetyl-β-glucosaminidase | – |
| α-mannosidase | – |
| α-fucosidase | – |

TABLE 5

Purification procedure of the extract obtained from the culture incubated with L-[2,3,4,5,6-³H]phenylalanine

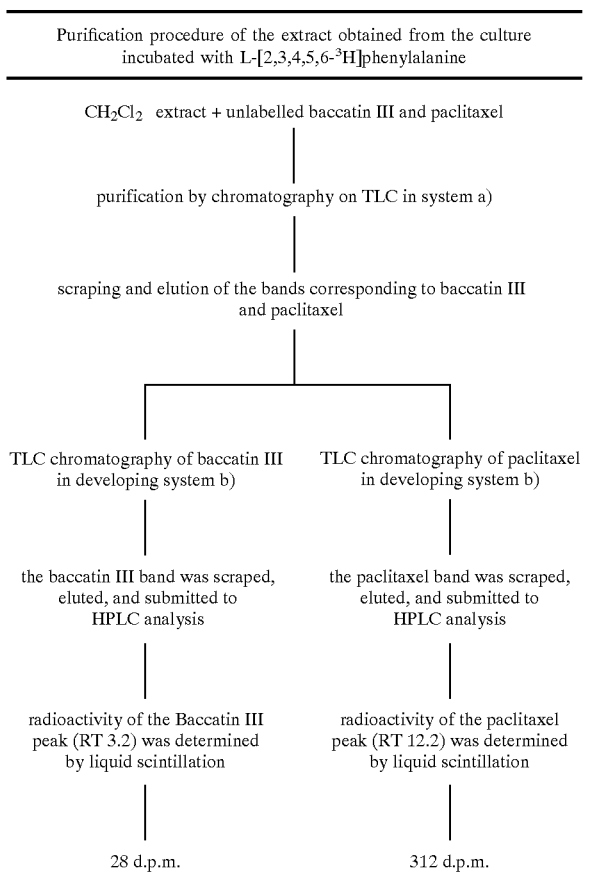

TABLE 5-continued

Purification procedure of the extract obtained from the culture incubated with L-[2,3,4,5,6-³H]phenylalanine TLC systems: a) TLC plates silica gel 60 (E. Merck, 64271 Darmstadt, Germany developed in n-hexane:acetone (1:1); b) TLC plates silica gel 60 developed in $CH_3CN:CH_2Cl_2$ (35:65).
HPLC system: as described in the Example 12.

What is claimed is:

1. A biologically pure culture of a microorganism belonging to the genus Kitasatosporia, which produces a taxane.

2. The microorganism according to claim 1 which produces a taxane selected from the group consisting of paclitaxel, 10 deacetyltaxol, 7-xylosyltaxol, 7-epi-10-deacetyltaxol, 7-xylosyl-10-deacetyltaxol, 7-epi-taxol, 7-epi-10-deacetylbaccatin III, baccatin III, 10-deacetyl baccatin III, cephalomannine and 10-deacetylcephalomannine.

3. The microorganism according to claim 1 which produces paclitaxel.

4. The microorganism according to claim 1 which produces a taxane which binds to an antibody specific for paclitaxel.

5. The microorganism according to claim 1 which produces a taxane which binds to antibody R4, 8A10, 3C6 or 3H5.

6. A biologically pure culture of Kitasatosporia sp. CECT 4991.

* * * * *